US006703042B1

(12) United States Patent
Buonato

(10) Patent No.: US 6,703,042 B1
(45) Date of Patent: Mar. 9, 2004

(54) SALTS OF L-CARNITINE AND LOWER ALKANOYL L-CARNITINE

(75) Inventor: Atonietta Buononato, Rome (IT)

(73) Assignee: Sigma-Tau Industries Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/979,880

(22) PCT Filed: May 26, 2000

(86) PCT No.: PCT/IT00/00217

§ 371 (c)(1),
(2), (4) Date: Nov. 27, 2001

(87) PCT Pub. No.: WO00/73258

PCT Pub. Date: Dec. 7, 2000

(30) Foreign Application Priority Data

May 28, 1999 (IT) ........................................ RM99A0339

(51) Int. Cl.⁷ ............................ A61K 9/20; A61K 9/48; A61K 9/14

(52) U.S. Cl. ........................ 424/444; 424/451; 424/463; 424/489; 562/561; 562/562; 562/563

(58) Field of Search .................................. 562/561, 562, 562/563; 424/463, 451, 489, 442

(56) References Cited

U.S. PATENT DOCUMENTS 6,306,392 B1 * 10/2001 Cavazza .................. 424/93.51

FOREIGN PATENT DOCUMENTS

| EP | 0 150 688 A | 8/1985 |
| EP | 0 167 115 A | 1/1986 |
| EP | 0 354 848 A | 2/1990 |
| WO | WO 98 47857 A | 10/1998 |

* cited by examiner

*Primary Examiner*—Jyothsna Venkat
(74) *Attorney, Agent, or Firm*—Nixon & Vanderhye P.C.

(57) ABSTRACT

The present invention relates to stable, non-hygroscopic salts of L-carnitine and lower alkanoyl L-carnitine endowed with enhanced nutritional and /or therapeutical efficacy with respect to their inner salts congeners and tom solid compositions containing such salts particularly suited to oral administration.

11 Claims, 1 Drawing Sheet

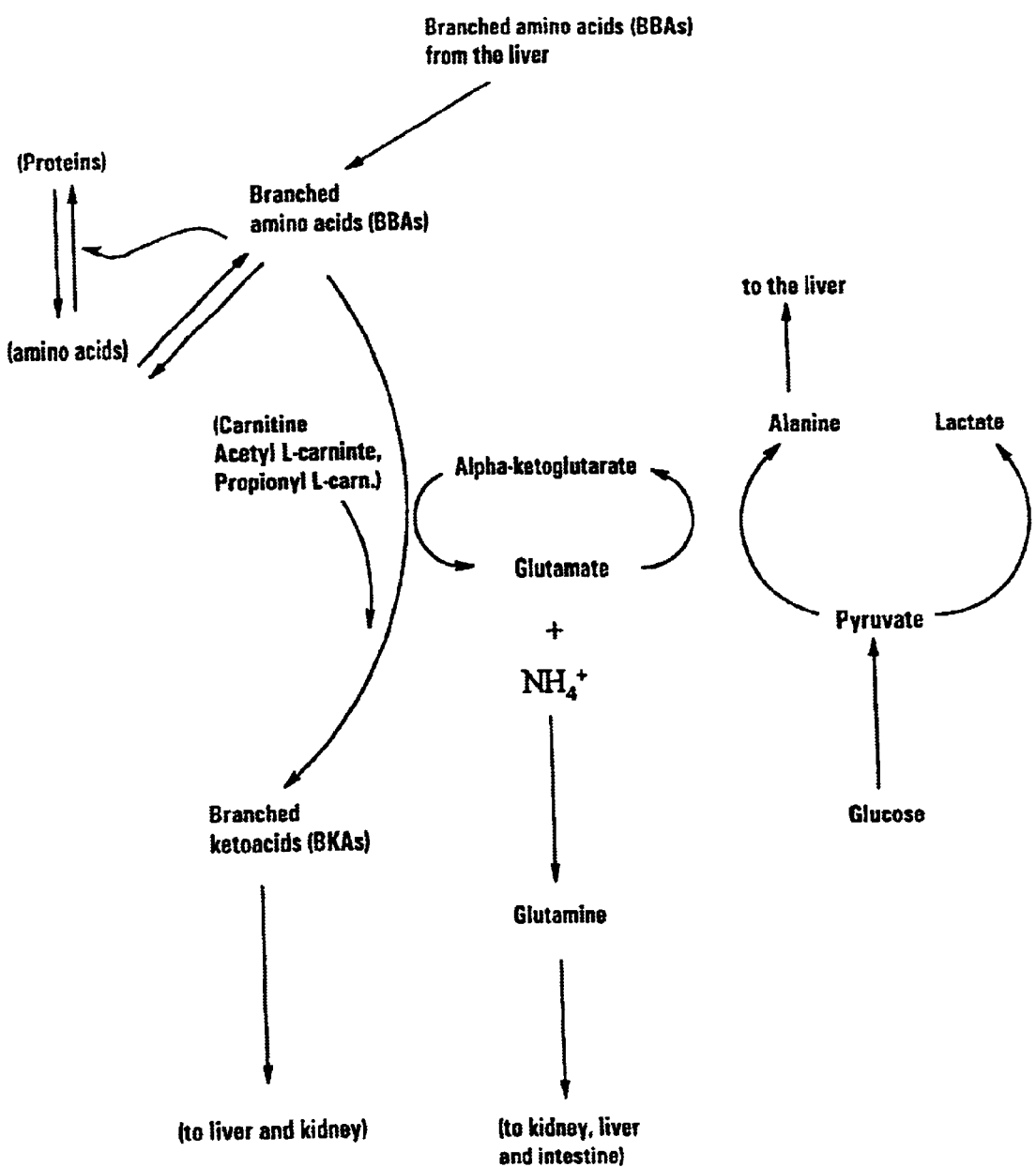

SALTS OF L-CARNITINE AND LOWER ALKANOYL L-CARNITINE

This application is a 371 of PCT/IT00/00217 filed on May 26, 2000.

The present invention relates to stable, non-hygroscopic salts of L-carnitine and lower alkanoyl L-carnitine endowed with enhanced nutritional and/or therapeutical efficacy with respect to their inner salts congeners and to solid compositions containing such salts, particularly suited to oral administration.

It has long since known that carnitine and its alkanoyl derivatives lend themselves to various therapeutical utilizations such as e.g. in the cardiovascular field for the treatment of acute and chronic myocardial ischaemia, angina pectoris, heart failure and cardiac arrhythmias. Acetyl L-carnitine is used in the neurologic field for the treatment of both central nervous system disturbances and peripheral neuropathies, particularly diabetic peripheral neuropathy. Propionyl L-carnitine is used for the treatment of chronic arteriosclerosis obliterans, particularly in patients showing the symptom of severely disabling intermittent claudication.

On the other hand, a widespread promotion of carnitine and derivatives thereof has rapidly been taking place towards utilizations other than those purely therapeutical, ever though allied to them.

It has, in fact, been widely recognized that in professional athletes as well as in any subject practising sport at amateur level, L-carnitine supplies energy to the skeletal musculature and increases the resistance to prolonged, intense stress, enhancing the performance capability of such individuals.

In addition, L(-)-carnitine or its lower alkanoyl derivatives constitute indispensable nutritional supplements for both vegetarians, whose diets have a low carnitine content as well as a low content of the two amino acids, lysine and methionine (the precursors of the biosynthesis of L(-)-carnitine in the kidneys and liver) and those subjects who have to live on a diet poor in protein for prolonged periods of time.

Consequently, various compositions containing carnitine or derivatives thereof, either as single components or in combinations with further active ingredients, have recently reached the market of the dietary supplements, health foods, energy foods and similar products.

It has long since been known that L(-)-carnitine and its alkanoyl derivatives are extremely hygroscopic and not very stable when they occur as inner salts (or "betaines") as represented by the formula

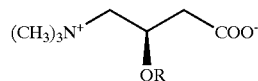

wherein R=H or $C_1$–$C_5$ lower alkanoyl.

This leads to complex problems of processing, stability and storage both of the raw materials and of the finished products. For example, L(-)-carnitine tablets have to be packaged in blisters to keep them out of contact with the air, since, otherwise, even in the presence of normal humidity conditions, they would undergo alterations, swelling up and becoming pasty and sticky.

Since the salts of L(-)-carnitine and its alkanoyl derivatives known to-date present the same therapeutic, nutritional or dietetic activities, respectively, as the so-called inner salts (or "betaines"), the problem of the hygroscopicity of the inner salts has tentatively been solved by salifying them with "pharmacologically acceptable" acids, which do not present unwanted toxic or side effects.

There is now an extensive body of literature, particularly patents, disclosing the production of such stable, non-hygroscopic salts.

Among L-carnitine salts, particularly L-carnitine tartrate and L-carnitine acid fumarate have to-date found practical utilization.

Although the aforesaid "pharmacologically acceptable" salts solve the problem of the hygroscopicity of L-carnitine inner salt more or less satisfactorily, in none of the known salts the anion moiety co-operates to enhance the nutritional, energetic and/or therapeutical efficacy which can be attributed to the "carnitine" moiety of the salts themselves.

Furthermore, none of the acids used for producing non-hygroscopic L-carnitine salts is capable of forming non-hygroscopic salts of alkanoyl L-carnitine. Thus, for example, whereas L(-)-carnitine acid fumarate and L(-)-carnitine tartrate are non-hygroscopic compounds, acetyl L(-)-carnitine acid fumarate and tartrate, respectively, are strongly hygroscopic compounds, which present the same drawbacks as the corresponding inner salt.

L-carnitine and acyl L-carnitine derivatives with aminoacids are already known.

EP-A1-0 150 688 discloses acetyl L-carnitine acid L-aspartate which is reported as a non-hygroscopic salt.

EP-A2-0 167 115 discloses condensation products of L-carnitine or acyl L-carnitine with an optically active acid aminoacid monosalified with potassium ion. Potassium-salified glutamic and aspartic acids are mentioned and preparation of L-carnitine potassium aspartate is exemplified.

Finally, EP-A1-0 354 848 discloses pharmaceutical compositions comprising L-carnitine lysinate as active ingredient, whose preparation and physico-chemical characterization are not reported.

Neither EP-A2-0 167 115 nor EP-A1-0 354 848 disclose whether the aforesaid L-carnitine derivatives are hygroscopic or non-hygroscopic The object of the present invention is to provide stable, non-hygroscopic salts of L-carnitine and lower alkanoyl L-carnitine which possess an enhanced therapeutical and/or nutritional efficacy with respect to the corresponding inner salts.

It is, therefore, apparent that the utility of the salts of the present invention is to be found not only in their lack of hygroscopicity and higher stability with respect to their corresponding inner salts, but also insofar as their anion moiety contributes to the nutritional, energetic and/or therapeutic efficacy of the salt as whole. The aforesaid efficacy of these novel salts is, therefore, not to be attributed exclusively to the "carnitine" moiety of the salt.

The aforesaid object, is achieved by the salts of L-carnitine and alkanoyl L-carnitine with amino acids having the formula (I):

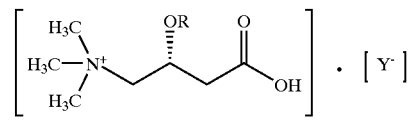

wherein:
R is hydrogen or a straight or branched-chain alkanoyl group having 2–5 carbon atoms; and
Y is the anion of an amino acid occurring in proteins selected from the group consisting of: leucine, isoleucine, vahine, cysteine, arginine, glutamic acid, glutamine, asparagine, glycine, alanine, threonine, serine, proline, hystidine, methionine, phenylalanine and tryptophane.

By "amino acid occurring in proteins" is meant any one of the twenty amino acids which are obtained via controlled hydrolysis of naturally occurring proteins (see, e.g., J. David Rawn, *Biochemistry*, Chapter 3 "Amino acids and the primary structure of proteins"; McGraw-Hill, 1990).

The anion $Y^-$ can optionally be salified at the amino group, preferably with a hydrohalogen acid such as hydrochloric acid or phosphoric acid.

When R is an alkanoyl group, it is preferably selected from the group consisting of acetyl, propionyl, butyryl, valeryl and isovaleryl.

Whilst in order to illustrate the nutritional and therapeutic efficacy of the amino acids in general reference is made to the conspicuously vast literature published to-date on this matter (see, e.g., F. Fidanza and G. Liguori, *Nutrizione umana*, Chapter 3: "Le proteine", Casa Editrice Libraria Idelson, 1995; and I. Goldberg (Ed.), *Functional Foods*, Chapter 12, "Amino acids, peptides and proteins" Chapman & Hall, Inc. 1994), it is deemed useful to briefly address the topic of the essential amino acids, in view of their peculiar role, and, among these, of the branched-chain amino acids.

It has long since been known that out of the nine essential amino acids (i.e. those normally occurring in proteins which can not be synthesized by the organism and must therefore be supplemented through the diet), the branched-chain amino acids (BAA) valine, leucine and isoleucine stimulate protein synthesis in skeletal muscle and liver. It is also well known that skeletal muscle is the main site for the initial step in BAAs catabolism resulting in energy production.

With reference to the attached figure which illustrates in a simplified form the relationships between proteins and amino acids within muscle cells, the first metabolic reaction in BAAs oxidative catabolism is transamination, i.e. the transaminase-regulated transfer of an α-amino group resulting in the formation of a branched-chain α-ketoacid (BKA) and a different amino acid. The BKA can either acquire an amino group, thus changing into a BAA again or be further and irreversibly catabolized resulting in energy production. The BKAs are catabolized in this way to a lesser extent within muscle cells. Most of BKAs are exported from muscle via the bloodstream to other organs (such as liver and kidneys) where BKAs are catabolized or re-aminated.

It is well known that strenuous exercise increases BAAs oxidation. In fact, it has been demonstrated that the skeletal musculature of resting well-trained sportsmen oxidizes more BAAs than the musculature of non-trained individuals. It has, furthermore, been shown that the BAAs oxidized by skeletal muscle during physical exercise derive from muscle proteins which are degraded during exercise as well as from the BAAs which are conveyed to the muscle via the bloodstream. The major source of the BAAs delivered via the bloodstream during exercise is the liver.

It is also known that exercise brings about transient periods which extend beyond the exercise, wherein the normal balance of protein synthesis to protein degradation in skeletal muscle has been shifted towards a relative increase in protein degradation. In conclusion, strenuous exercise causes the muscle to use up a portion of its own protein structure.

It has been clearly shown that the quantitative contribution of protein oxidation to the increased energy demand caused by the exercise is relatively small. Nevertheless, BAAs oxidation may be significant insofar as their oxidation generates the amino acids alanine and glutamine which can be exported from muscle to other sites where they are used as energy sources. Alanine is carried via the bloodstream to the liver where it contributes to the formation of glucose, which is the preferred "fuel" of the brain, whilst glutamine is an energy source for the kidneys and intestine. It is, therefore, apparent that the increased oxidation of proteins and BAA during exercise is an obligatory event.

One of the functions of BAAs oxidation in the muscle during exercise is the removal of lactate from muscle. In fact, it is well known that the muscle under strenuous exercise burns glucose in a substantially anaerobic manner, resulting in the formulation of lactate which derives directly from pyruvate. Lactate build-up in the muscle is associated with muscle fatigue and onset of muscular cramps and should, therefore, be avoided.

With reference to the figure, the amino groups of BAAs are transferred, via the α-ketoglutarate/glutamate cycle, to pyruvate, resulting in the formation of alanine. Alanine is transferred to the liver where it contributes to glucose synthesis. The pyruvate portion which is involved in alanine synthesis is not converted to lactate. Therefore, BAAs oxidation serves to modulate lactate build-up in skeletal muscle.

Moreover, hydrogen ions from catabolic reactions must be removed, so as to avoid any risk of a pH decrease. Hydrogen ions are removed from muscle by combining (in the form of ammonium ion) with glutamate resulting in glutamine. When taken up by the kidney, ammonium ions (and, hence, hydrogen ions) are extracted with urine.

It is also well known that during strenuous exercise a net loss of BAAs takes place in the liver whilst the skeletal muscle concomitantly takes up BAAs from bloodstream. Therefore, the increased oxidation of BAAs in muscle cells seems to cause a loss in BAAs from liver proteins. It has been further noticed that the rate of protein breakdown in the liver can be partly hindered by amino acids, in particular glutamine. It was in particular noticed that an increased amount of glutamine is exported from liver during exercise which may be related to the effect of this amino acid on protein synthesis.

The following non-limiting examples show the preparation and physico-chemical features of some salts according to the present invention.

EXAMPLE 1

Acetyl L-carnitine L-isoleucinate hydrochloride (BS/208)

Acetyl L-carnitine Chloride, M.w. 239, m.p. 135° C. (dec.) L-isoleucine, M.w. 131, m.p. 284° C.

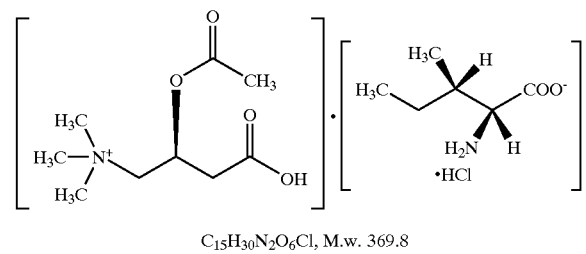

$C_{15}H_{30}N_2O_6Cl$, M.w. 369.8

23.9 g (0.1 moles) of acetyl L-carnitine chloride were dissolved in 300 mL of distilled water. To the resulting solution 13.1 g (0.1 moles) of L-isoleucine were added with stirring. Following complete dissolution, 300 mL of isobutanol were added and the resulting mixture concentrated under vacuum at 40° C. The residue thus obtained was taken up with ethyl acetate and the resulting mixture left under magnetic stirring. After eight hours, when the whole product was finely crumbled, it was filtered under vacuum on a Gooch No. 4. The solid thus obtained was washed with ethyl acetate and dried in a thermostatic oven at 40° C. overnight.

34 g of the title compound were obtained. Yield 95%. Melting point: 170° C. (dec.). The compound was non-hygroscopic.

The following analysis were carried out:

| HPLC; NMR; DSC; $[\alpha]_D^{20}$; K.F.; E.A.; pH. | | | | |
|---|---|---|---|---|
| K. Fischer: 1.1% | | | | |
| Elementary Analysis | C % | H % | N % | Cl % |
| Calculated | 48.7 | 8.17 | 7.57 | 9.58 |
| Found | 48.9 | 8.15 | 7.61 | 9.53 | pH: 3.6(c=0.5% H$_2$O); $[\alpha]_{20}^D$=−12.4 (c=0.5% H$_2$O; NMR D$_2$O δ=5.6–5.5 (1H, m, (CH—CO); 3.9–3.6 (2H, m, CH$_2$—N; 3.6–3.5 (1H, d, CH—NH$_2$); 3.2–3.1 (9H, s, (CH$_3$)$_3$N); 2.7–2.4 ; (2H, m, CH$_2$—COO); 2.1 (3H, s, CO—CH$_3$); 2–1.9 (1H, m, CH—CH—NH$_2$); 1.6–1.1 (2H, m, CH$_2$—$_{CH3}$); 1–0.9 (3H, d, CH—CH); 0.9–0.8 (3H, t, CH$_3$—CH$_2$).

| HPLC: | |
|---|---|
| Column: | Hypersil APS-2 (5 μm) 250 × 4 |
| Temperature: | =30° C. |
| Eluant: | KH$_2$PO$_4$/CH$_3$CN (65–35 v/v) 0.05M |
| pH: | 4.7 with H$_3$PO$_4$ |
| Flow rate: | 0.7 mL/min |
| Acetyl L-carnitine: | R$_t$ = 8.5 |
| L-isoleucine: | R$_t$ = 5.8 |
| Ratio: | acetyl L-carnitine 55%; L-isoleucine 35.5% |

EXAMPLE 2

Propionyl L-carnitine L-leucinate Hydrochloride (BS/209)

Propionyl L-carnitine Chloride, M.w. 253, m.p. 175° C. (dec.) L-leucine, M.w. 131, m.p. 293° C.

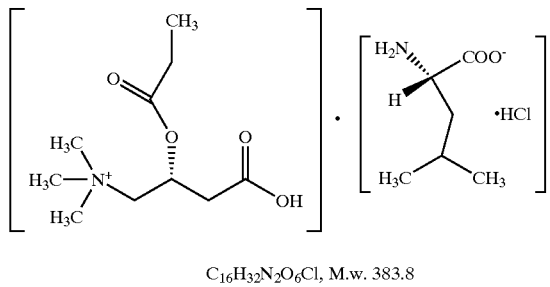

C$_{16}$H$_{32}$N$_2$O$_6$Cl, M.w. 383.8

25.3 g (0.1 moles) of propionyl L-carnitine chloride were dissolved in 400 mL of distilled water at 40° C. and to the resulting solution 13.1 g (0.1 moles) of L-leucine were added under stirring. Following complete dissolution, the mixture was concentrated moles vacuum at 40° C. in a rotating evaporator with water pump at 20 mm/Hg. When the concentration was completed, the mixture was taken up with isopropanol and concentrated again till complete dryness.

The resulting residue was taken up with ethyl acetate and left under magnetic stirring. After one hour, when the whole product was crumbled, it was filtered under vacuum on Gooch No. 4. The solid thus obtained was washed with ethyl acetate and dried in a thermostatic oven at 30° C. overnight.

36 g of the title compound were obtained. Yield 95% Melting point: 161° C. (dec). The compound was non-hygroscopic.

The following analyses were carried out: NMR; DSC; M.P.; $[\alpha]_D^{20}$; K.F.; E.A.; pH. K. Fischer: 1.4%; pH: 3.7 (c=0.5% H$_2$O); $[\alpha]_D^{20}$=−12.88 (c=0.5% H$_2$O); NMR D$_2$O δ=5.6–5.5 (1H, m, CH—OCO); 3.8–3.7(1H, t, CH—NH$_2$); 3.7–3.6 (2H, M, CH$_2$—N); 3.2 (9H, s,(CH$_3$)$_3$—N); 2.8–2.7 (2H, q, CH$_2$—CH$_3$); 2.7–2.5 (2H, m, CH$_2$—COOH); 1.8–1.7 (2H, t, CH$_2$—CH); 1.7–1.5 (1H, m, CH); 1.1–1 (3H, t, CH$_3$—CH$_2$); 1–0.9 (6H, d, CH$_3$CH$_3$—CH);

| Elementary Analysis | C % | H % | N % | Cl % |
|---|---|---|---|---|
| Calculated | 50.06 | 8.4 | 7.3 | 9.24 |
| Found | 49.98 | 8.31 | 7.27 | 9.21 |

EXAMPLE 3

L-carnitine L-valinate Phosphate (BS/204)

L-carnitine Inner Salt M.w. 161, m.p. 197–198° C. L-valine, M.w. 117, m.p. 315° C.

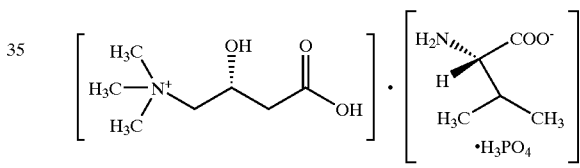

C$_{12}$H$_{28}$N$_2$O$_9$P, M.w. 375.3

16.1 g (0.1 moles) of L-carnitine inner salt were dissolved in 300 mL of distilled water and to the resulting solution 11.7 (0.1 moles) of L-valine and 7.5 mL of 85% phosphoric acid (0.1 moles) were added.

Following complete dissolution, 300 mL of isobutanol were added and the whole mixture concentrated under vacuum at 40° C. in a rotating evaporator with water pump at 25 mm/Hg. The residue thus obtained was taken up with ethyl acetate and left under magnetic stirring. When the whole product was crumbled, it was filtered under vacuum on a Gooch No. 4. The solid thus obtained was washed with ethyl acetate and dried in a thermostatic oven at 30° C. overnight.

32 g of the title compound were obtained. Yield 96%. Melting point 229° C. (dec.). The compound was non-hygroscopic.

The following analysis were carried out: NMR; DSC; $[\alpha]_D^{20}$; K.F.; E.A.; pH; HPLC. K. Fischer: 0.5%; $[\alpha]_D^{20}$=−10.1 (c=0.5% H$_2$O); pH: 3.5 (c=0.5% H$_2$O); NMR D$_2$O δ=4.6–4.5 (1H, m, CH—OH); 3.7–3.6 (1H, CH—CH—NH$_2$); 3.5–3.4 (2H, d, CH$_2$—N); 3.3 (9H, s, (CH$_3$)$_3$—N); 2.5–2.4 (2H, d, CH$_2$—COO); 2.3–2.2 (1H, m, CH—CH); 1.1–1 (6H, d, CH$_3$CH$_3$—CH);

| Elementary Analysis | C % | H % | N % | P % |
|---|---|---|---|---|
| Calculated | 38.40 | 7.52 | 7.46 | 8.25 |
| Found | 33.29 | 7.61 | 7.39 | 8.21 |

HPLC:

| | |
|---|---|
| Column: | Hypersil APS-2 (5 μm) 250 × 4 |
| Temperature: | =30° C. |
| Eluant: | KH$_2$PO$_4$/CH$_3$CN (65–35 v/v) 0.05M |
| pH: | 4.7 with H$_3$PO$_4$ |
| Flow rate: | 0.7 mL/min |
| L-carnitine: | R$_t$ = 10.1 |
| L-valine: | R$_t$ = 5.2 |

EXAMPLE 4

Acetyl L-carnitine L-cysteinate Hydrochloride (85/197)

Acetyl L-carnitine Inner Salt, M.w. 203, m.p. 140–141° C. (dec.). Very Hygroscopic. L-cysteine Hydrochloride, M.w. 157.6, m.p. 170° C. (dec.). Very Hygroscopic.

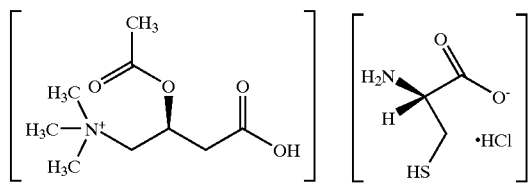

C$_{12}$H$_{25}$N$_2$O$_6$S, M.w. 360.85

20.3 g (0.1 moles) of acetyl L-carnitine inner salt were dissolved in 50 mL of distilled water and to the resulting solution 15.7 g (0.1 moles) of L-cysteine hydrochloride were added under stirring.

Following complete dissolution, the whole mixture was concentrated under vacuum at 40° C. in a rotating evaporator with water pump at 25 mm/Hg, added with isobutanol and subjected to azoetropic distillation. The residue thus obtained was taken up with a solvent such as acetone or ethyl acetate and the resulting mixture left under mechanical stirring overnight. The resulting mixture was filtered under vacuum on a Gooch No. 4. The solid thus obtained was dried under vacuum in a thermostatic oven at 30° C. overnight.

33.5 g of the title compound having melting point 184° C. (dec.) were obtained. Yield 96%. The compound occurred as a white, crystalline, non-hygroscopic solid.

The following analysis were carried out: NMR; M.P.; R.P.; E.A.; pH; K.F. K.F.=0.6%; $[\alpha]_D^{20}$=−11.5 (c=1% H$_2$O); pH: 3.9 (c=1% H$_2$O);

| Elementary Analysis: | C % | H % | N % | Cl % | S % |
|---|---|---|---|---|---|
| Calculated | 39.94 | 6.98 | 7.76 | 9.82 | 8.88 |
| Found | 39.81 | 7.11 | 7.69 | 9.79 | 8.83 |

NMR D$_2$O δ=5.5–5.4 (1H, m, —C$\underline{H}$—); 4.5–4.3 (1H, t, C$\underline{H}$—NH$_2$); 3.8–3.5 (2H, m, N—C$\underline{H}_2$); 3.3–3.2 (2H, d, CH$_2$—SH); 3.1 (9H, s, N—(C$\underline{H}_3$)$_3$); 2.7–2.5 (2H, m, —C$\underline{H}_2$—COOH); 2 (3H, s, COC$\underline{H}_3$).

EXAMPLE 5

Acetyl L-carnitine L-arginate Hydrochloride (BS/207)

Acetyl L-carnitine Chloride, M.w. 239, m.p. 135° C. (dec.) L-arginine Hydrochloride, M.w. 210.67, m.p. 226° C.

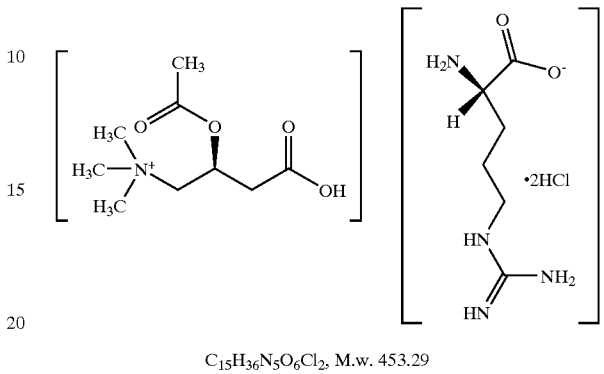

C$_{15}$H$_{36}$N$_5$O$_6$Cl$_2$, M.w. 453.29

23.9 g (0.1 moles) of acetyl L-carnitine chloride were dissolved in 100 mL of distilled water and to the resulting solution 21 g (0.1 moles) of L-arginine hydrochloride were added.

Following complete dissolution, the whole mixture was concentrated under vacuum at 40° C. in a rotating evaporator with a water pump at 25 mm/Hg, added with isobutanol and subjected to azoetropic distillation. The residue obtained after the concentration was taken up with a solvent such as acetone or ethyl acetate and the mixture left under mechanical stirring overnight. The mixture was then filtered on a Gooch No. 4. The solid thus obtained was dried under vacuum in a thermostatic oven at 30° C. overnight.

41 g of the title compound were obtained as a white, crystalline, non-hygroscopic solid. Yield 95%. Melting point 194° C. (dec.).

The following analysis were carried out: NMR; M.P.; R.P.; E.A.; pH; K.F. K.F.=0.8%; $[\alpha]_D^{20}$=−6.1 (c=1% H$_2$O); pH: 3.6 (c=1% H$_2$O);

| Elementary Analysis | C % | H % | N % | Cl % |
|---|---|---|---|---|
| Calculated | 39.74 | 8.00 | 15.45 | 15.64 |
| Found | 39.52 | 8.11 | 15.71 | 15.47 |

NMR D$_2$O δ=5.5–5.4 (1H, m, —C$\underline{H}$—); 3.8–3.5 (2H, m, N—C$\underline{H}_2$); 3.1 (9H, s, N—(C$\underline{H}_3$)$_3$); 3.1–3 (1H, t, C$\underline{H}$—NH$_2$); 3–2.9 (2H, q, CH$_2$—C$\underline{H}_2$—CH$_2$); 2.7–2.5 (2H, m, —C$\underline{H}_2$—COOH); 2 (3H, s, CO—C$\underline{H}_3$); 1.5–1.4 (4H, m, C$\underline{H}_2$—CH$_2$—C$\underline{H}_2$);

HPLC:

| | |
|---|---|
| Column: | Hypersil APS-2 (5 μm) 250 × 4.6 |
| Temperature: | =30° C. |
| Mobile phase: | CH$_3$CN/H$_2$O + KH$_2$PO$_4$/CH$_3$CN 0.05M (65–35 v/v) |
| pH: | 4.7 with H$_3$PO$_4$ |
| Flow rate: | 1 mL/min |
| L-carnitine: | R$_t$ = 7.9 |
| L-arginine: | R$_t$ = 15.9 |

EXAMPLE 6

Acetyl L-carnitine L-glutamate Hydrochloride (BS/205)

Acetyl L-carnitine Inner Salt, M.w. 203, m.p. 145° C. (dec.)
L-glutamic Acid Hydrochloride, M.w. 183.59, m.p. 205° C.

The procedures of Example 5 were repeated, using L(+)-glutamic acid hydrochloride, obtaining the following non-hygroscopic compound.

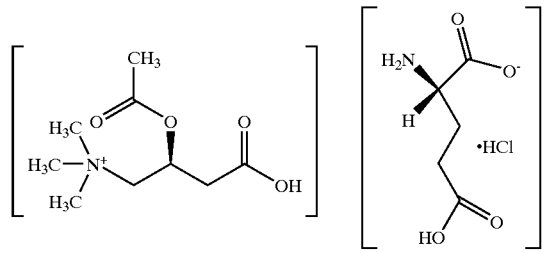

$C_{14}H_{26}N_2O_8Cl$, M.w. 385.8

Yield: 96%. m.p.: 185° C. (dec.); K.F.=0.5%; $[\alpha]_D^{20}$=−6.6 (c=1% $H_2O$); pH: 3.7 (c=0,5% $H_2O$);

| Elementary Analysis | C % | H % | N % | Cl % |
|---|---|---|---|---|
| Calculated | 43.58 | 6.8 | 7.25 | 9.2 |
| Found | 43.2 | 7.02 | 7.11 | 8.98 |

NMR $D_2O$ δ=5.5–5.4 (1H, m, —C<u>H</u>—); 3.8–3.5 (2H, m, N—C<u>H</u>$_2$); 3.7–3.6 (1H, t, C<u>H</u>—NH$_2$); 3.1 (9H, s, N—(CH$_3$)$_3$); 2.7–2.5 (2H, m, —C<u>H</u>$_2$—COOH); 2.5–2.4 (2H, t, —CH$_2$—C<u>H</u>$_2$—COOH); 2 (3H, s, CO—C<u>H</u>$_3$); 2–1.9 (2H, q, CH—C<u>H</u>$_2$—CH$_2$).

| HPLC: | |
|---|---|
| Column: | Hypersil APS-2 (5 μm) 250 × 4.6 |
| Temperature: | =30° C. |
| Mobile phase: | CH$_3$CN/H$_2$O + KH$_2$PO$_4$/CH$_3$CN 0.05M (65–35 v/v) |
| pH: | 4.7 with H$_3$PO$_4$ |
| Flow rate: | 1 mL/min |
| Acetyl L-carnitine: | R$_t$ = 7.9 |
| L-glutamic acid: | R$_t$ = 10.5 |

EXAMPLE 7

Acetyl L-carnitine L-glutaminate Hydrochloride (BS/185)
Acetyl L-carnitine Chloride, M.w. 239, m.p. 135° C.
L-glutamine M.w. 140.15, m.p. 185–186° C.

The procedures of Example 1 were repeated, using L-glutamine, thus obtaining the following compound which occurred as a white, crystalline, non-hygroscopic solid. Yield 95%.

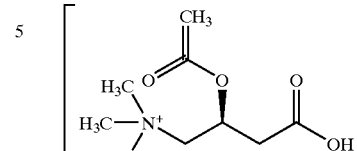

$C_{14}H_{28}N_3O_7Cl$, M.w. 385.83 m.p.: 189° C. (dec.); K.F.=0.5%; $[\alpha]_D^{20}$=−6.1 (c=1% $H_2O$); pH: 3.2 (c=1% $H_2O$);

| Elementary Analysis | C % | H % | N % | Cl % |
|---|---|---|---|---|
| Calculated | 44.58 | 7.28 | 10.9 | 9.18 |
| Found | 44.49 | 7.19 | 11.08 | 9.07 |

NMR $D_2O$ δ=5.5–5.4 (1H, m, —C<u>H</u>—); 3.8–3.5 (2H, m, N—C<u>H</u>$_2$); 3.7–3.6 (1H, t, C<u>H</u>—NH$_2$); 3.1 (9H, s, N—(CH$_3$)$_3$); 2.7–2.5 (2H, m, —CH$_2$—COOH); 2.5–2.4 (2H, C<u>H</u>$_2$CONH$_2$); 2.1–2 (2H, C<u>H</u>$_2$—CH); 2 (3H, s, COC<u>H</u>$_3$).

EXAMPLE 8

Acetyl L-carnitine L-aspartate Hydrochloride (BS/193)

Acetyl L-carnitine chloride, M.w. 239, m.p. 135° C. (dec.)
L-aspartic acid, M.w. 133.1, m.p. 270° C. (dec.)

The procedures of Example 1 were repeated, using L-aspartic acid, thus obtaining the following non-hygroscopic compound. Yield 96%.

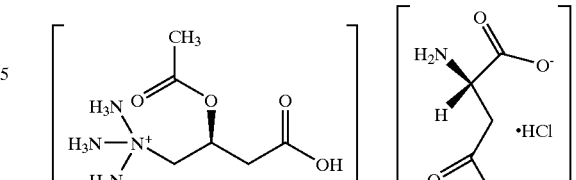

$C_{13}H_{26}N_2O_8Cl$, M.w. 373.79 m.p.: 196° C. (dec.); K.F.=0.4%; $[\alpha]_D^{20}$=−5.6 (c=1% $H_2O$); pH: 3.6 (c=1% $H_2O$);

| Elementary Analysis | C % | H % | N % | Cl % |
|---|---|---|---|---|
| Calculated | 41.77 | 7.01 | 7.5 | 9.48 |
| Found | 41.55 | 6.89 | 7.69 | 9.37 |

NMR $D_2O$ δ=5.5–5.4 (1H, m, —C<u>H</u>—); 3.8–3.5 (2H, m, N—C<u>H</u>$_2$); 3.4–3 (1H, t, C<u>H</u>—NH$_2$); 3.1 (9H, s, N—(CH$_3$)$_3$); 2.7–2.5 (2H, m, —C<u>H</u>$_2$—COOH); 2.5–2 (2H, m, —C<u>H</u>$_2$CH); 2 (3H, s, COC<u>H</u>$_3$)

| HPLC: | |
|---|---|
| Column: | Hypersil APS-2 (5 μm) 250 × 4.6 |
| Temperature: | =30° C. |
| Mobile phase: | CH$_3$CN/H$_2$O + KH$_2$PO$_4$/CH$_3$CN 0.05M (65–35 v/v) |
| pH: | 4.7 with H$_3$PO$_4$ |
| Flow rate: | 1 mL/min |
| Acetyl L-carnitine: | R$_t$ = 7.9 |
| L-aspartic acid: | R$_t$ = 9.1 |

EXAMPLE 9

Acetyl L-carnitine L-asparaginate Hydrochloride (BS/194)

Acetyl L-carnitine Chloride, M.w. 239, m.p. 135° C. (dec.)
L-asparagine, M.w. 150.14, m.p. 234–235° C.

The procedures of Example 1 were repeated, using L(+)-asparagine, thus obtaining the following compound which occurred as a white crystalline, non-hygroscopic solid. Yield 96%.

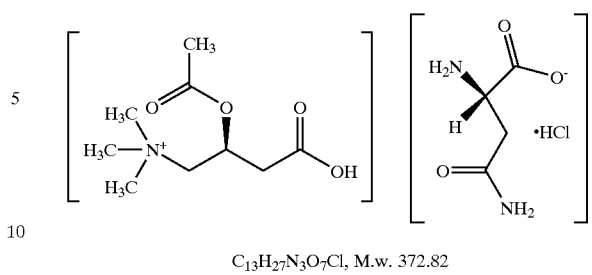

$C_{13}H_{27}N_3O_7Cl$, M.w. 372.82 m.p.: 180° C. (dec.); K.F.=0.4%; $[\alpha]_D^{20}$=−3.9 (c=1% H$_2$O); pH: 3.7 (c=0.5% H$_2$O);

| Elementary Analysis | C % | H % | N % | Cl % |
|---|---|---|---|---|
| Calculated | 41.88 | 7.3 | 11.27 | 9.5 |
| Found | 41.71 | 7.28 | 12.39 | 9.37 |

NMR D$_2$O δ=5.5–5.4 (1H, m, —C$\underline{H}$—); 3.8–3.5 (2H, m, N—C$\underline{H}_2$); 3.3–3.2 (1H, t, C$\underline{H}$—NH$_2$); 3.1 (9H, s, N—(C$\underline{H}_3$)$_3$); 2.7–2.5 (2H, m, —C$\underline{H}_2$—COOH); 2.5–2.1 (2H, m, —CH—C$\underline{H}_2$); 2 (3H, s, COC$\underline{H}_3$).

EXAMPLES 10–19

The compounds whose most relevant physico-chemical features are shown in the following Table 1 were prepared as described in Example 1, substituting for L-isoleucine an equimolar amount of the amino acid indicated in the column "Amino acid" of Table 1.

TABLE 1

Physico-chemical features of the compounds of Examples 10–19

Ex. $(CH_3)_3$—N$^+$—CH$_2$—CH—CH$_2$—COC  (OR, where R = H; COCH$_3$; COCH$_2$CH$_3$)

| Ex. | | AMINO ACID | M.w. | $[\alpha]_D^{20}$ C = 1% H$_2$O |
|---|---|---|---|---|
| 10 | R = COCH$_3$ | GLYCINE HYDROCHLORIDE | 331.52 | −14.9 |
| 11 | R = COCH$_3$ | L-ALANINE HYDROCHLORIDE | 328.55 | −7.1 |
| 12 | R = COCH$_3$ | L-THREONINE HYDROCHLORIDE | 357.57 | −24.3 |
| 13 | R = COCH$_3$ | L-SERINE HYDROCHLORIDE | 343.54 | −6.9 |
| 14 | R = COCH$_2$CH$_3$ | L-PROLINE HYDROCHLORIDE | 368.58 | −28.6 |
| 15 | R = H | L-HYSTIDINE HYDROCHLORIDE | 316.16 | −11.1 |
| 16 | R = H | L-METHIONINE HYDROCHLORIDE | 346.66 | −3.6 |
| 17 | R = COCH$_2$CH$_3$ | L-PHENYLALANINE HYDROCHLORIDE | 418.64 | −21 |
| 18 | R = H | L-LYSINE HYDROCHLORIDE | 307.19 | −5.8 |
| 19 | R = COCH$_3$ | L-TRYPTOPHANE HYDROCHLORIDE | 443.68 | −22.5 |

| Ex. | M.P. | pH C = 1% H$_2$O | N.M.R. |
|---|---|---|---|
| 10 | 176–78° C. | 2.98 | D$_2$O δ = 5.55–5.45(1H, m, C$\underline{H}$—); 3.8–3.5(2H, m, NC$\underline{H}_2$); 3.6(2H, s, C$\underline{H}_2$—NH$_2$); 3.1(9H, s, (CH$_3$)$_3$N); 2.7–2.5(2H, m, C$\underline{H}_2$—COOH) 2, (3H, s, COC$\underline{H}_3$) |
| 11 | 195–96° C. | 3.1 | D$_2$O δ = 5.55–5.45(1H, m, C$\underline{H}$—); 4–3.6(1H, q, C$\underline{H}$—CH$_3$); 3.8–3.6 (2H, m, N—C$\underline{H}_2$); 3.1(9H, s, N(C$\underline{H}_3$); 2.7–2.5(2H, m, C$\underline{H}_2$—COOH); 2(3H, s, COC$\underline{H}_3$); 1.6–1.5(3H, d, C$\underline{H}_3$—CH) |
| 12 | 193–95° C. | 2.9 | D$_2$O δ = 5.55–5.4(1H, m, C$\underline{H}$—); 4.4–4.2(1H, m, C$\underline{H}$—NH$_2$); 3.8–3.5(2H, m, N—C$\underline{H}_2$); 3.6–3.5(1H, d, C$\underline{H}_2$OH); 3.1(9H, s, N(C$\underline{H}_3$)$_3$); 2.7–2.5(2H, m, C$\underline{H}_2$—COOH); 2(3H, s, COC$\underline{H}_3$); 1.5–1.4(3H, d, C$\underline{H}_3$—CH) |
| 13 | 174–76° C. | 2.9 | D$_2$O δ = 5.55–5.45(1H, m, C$\underline{H}$—); 4.2–4(1H, m, C$\underline{H}$—NH$_2$); 4–3.9(2H, d, C$\underline{H}_2$CH); 3.8–3.5(2H, m, N—C$\underline{H}_2$); 3.1(9H, s, N(C$\underline{H}_3$)$_3$); 2.7–2.5(2H, m, C$\underline{H}_2$—COOH); 2(3H, s, (COC$\underline{H}_3$) |

TABLE 1-continued

Physico-chemical features of the compounds of Examples 10–19

| | | | |
|---|---|---|---|
| 14 | 201–203° C. | 2.89 | D$_2$O δ =5.6–5.5(1H, m, CH—OCO); 4.2–4(1H, t, CH—COOH); 3.7–3.6 (2H, m, CH$_2$—N); 3.6–3.4(2H, t, CH$_2$—NH); 3.2(9H, s, (CH$_3$)$_3$N); 2.8–2.7(2H, q, CH$_2$—CH$_3$); 2.7–2.5(2H, m, CH$_2$—COOH); 2.4–2(4H, m, CH$_3$—CH$_2$—CH); 1.1–1(1H, t, CH$_3$—CH$_2$) |
| 15 | 210–12° C. | 4.9 | D$_2$O δ = 7.6 (1H, s,  ); 6.8 (1H, s, 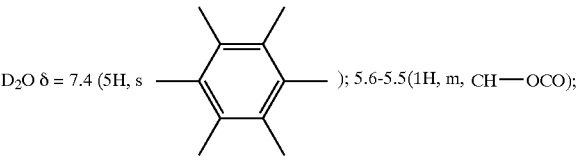 ) 4.6–4.5(1H, m, CH—OH); 3.7–3.5(1H, t, CH—CH$_2$); 3.5–3.4(2H, d, CH$_2$—N); 3.3(9H, s, (CH$_3$)$_3$—N); 3–2.9(2H, d, CH$_2$—CH); 2.5–2.4(2H, d, CH$_2$COOH) |
| 16 | 199–201° C. | 3.6 | D$_2$O δ = 4.6–4.5(1H, m, CH—OH); 4.4–4.1(1H, t, CH—NH$_2$); 3.5–3.4(2H, d, CH$_2$—N); 3.3(9H, s, (CH$_3$)$_3$N); 2.8–2.6(2H, t, SCH$_2$); 2.5–2.4(2H, t, CH$_2$—CH); 2.4–2.3(2H, d, CH$_2$—COOH); 2.1(3H, S—CH$_3$) |
| 17 | 208–209° C. | 3.15 | D$_2$O δ = 7.4 (5H, s 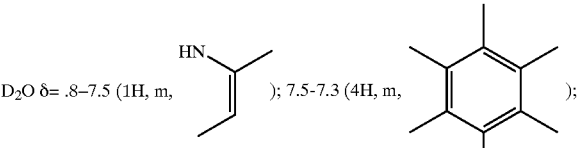 ); 5.6-5.5(1H, m, CH—OCO); 4.5–4.3(1H, t, CH—CH$_2$); 3.7–3.6(2H, m, CH$_2$—N); 3.4–3.2(2H, d, CH$_3$CH); 3.2(9H, s, (CH$_3$)$_3$N); 2.8–2.7(2H, q, CH$_2$—CH$_3$); 2.7–2.5(2H, m-CH$_2$ COOH); 1.1–1(3H, t, CH$_3$—CH$_2$) |
| 18 | 147–49° C. | 5.4 | D$_2$O δ = 4.6–4.5(1H, m, CH—OH); 3.9–3.7(1H, t, CH$_2$—NH$_2$); 3.5–3.4 (2H, d, CH$_2$—N); 3.5–3.4(2H, d, CH$_2$—N); 3.3–3(2H, t, CH$_2$—CH$_2$); 3.2 (9H, s, (CH$_3$)$_3$N); 2.4–2.3(2H, d, CH$_2$—COOH); 2.1–1.5(6H, m-(CH$_2$)$_3$—CH) |
| 19 | 197–98° C. | 2.95 | D$_2$O δ= .8–7.5 (1H, m, [structure] ); 7.5-7.3 (4H, m, [structure] ); 5.5–5.4(1H, m, —CH—); 4.6–4.4(1H, t, CH—CH$_2$); 3.8–3.5(2H, m, N—CH$_2$); 3.6–3.5(2H, d, CH$_2$—CH); 3.6–3.5(2H, d, CH$_2$—CH); 3.1(9H, s, N—(CH$_3$)$_3$); 2.7–2.5(2H, m, CH$_2$COOH); 2(3H, s, COCH$_3$) |

In the following Table 2 the increase in weight (%) and appearance of some compounds of the present invention are shown in comparison with the inner salts of L-carnitine and acetyl L-carnitine and the chlorides of acetyl and propionyl L-carnitine following exposure of the compounds to 70±5% relative humidity, at 25° C. for 24 hours.

TABLE 2

| Compound | Increase in weight (%) | Appearance |
|---|---|---|
| L-carnitine inner salt | 23 | deliquescent |
| Acetyl-L-carnitine inner salt | 19 | deliquescent |
| Acetyl-L-carnitine chloride | 8 | clumped mass |
| Propionyl-L-carnitine chloride | 15 | deliquescent |
| Example 1 (BS/208) | 0.2 | no variation |
| Example 2 (BS/209) | 0.25 | no variation |
| Example 3 (BS/204) | 0.1 | no variation |
| Example 4 (BS/197) | 0.6 | no variation |
| Example 5 (BS/207) | 0.45 | no variation |
| Example 6 (BS/205) | 0.4 | no variation |
| Example 7 (BS/185) | 0.6 | no variation |
| Example 8 (BS/193) | 0.7 | no variation |
| Example 9 (BS/194) | 0.3 | no variation |

In addition to the advantages of technological nature due to stability and lack of hygroscopicity, the salts of formula (I) present the further advantage for the consumer to make it easy the intake of a proper dose of the active ingredients, which can be; easily adjusted to suit the personal needs of a specific individual. The consumer compliance is thus greatly facilitated both in the therapeutic and dietetic field, such as e.g. in training diets, in the nourishment of debilitated and stressed individuals and in vegetarian diets.

For instance, the rational and protracted utilization of dietary supplements containing an effective amount of a salt of the present invention, allows the following favourable effects to be achieved:

(a) to spare muscle proteins and particularly the branched amino acids present in the skeletal muscle;

(b) to stimulate protein synthesis in skeletal muscle and liver;

(c) to provide amino groups for the synthesis of alanine and glutamine, both of which play a role in gluconeo-genesis;

(d) to enhance the metabolic conversion of pyruvate to alanine rather than lactate;

(e) to enhance hydrogen ion efflux from skeletal muscle via conversion of glutamate to glutamine so as to keep intramuscular pH at optimum value; and (f) to promote endurance and optimum performances in aerobic sport activities.

What is claimed is:

1. A salt of L-carnitine or alkanoyl L-carnitine with an amino acid, having the formula (I)

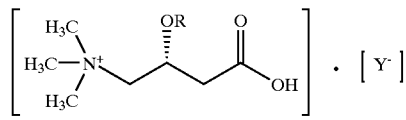

wherein:
R is hydrogen or a straight or branched-chain alkanoyl group of 2–5 carbon atoms; and
$Y^-$ is the anion of an amino acid occurring in proteins selected from the group consisting of leucine, isoleucine, valine, cysteine, arginine, glutamine, asparagine, glycine, alanine, threonine, serine, proline, hystidine, methionine, phenylalanine and tryptophane.

2. The salt of claim 1, salified at the amino group with an acid selected from the group consisting of hydrochloric, hydrobromic and phosphoric acid.

3. The salt of claim 1, wherein R is selected from the group consisting of acetyl, propionyl, butyryl, valeryl and isovaleryl.

4. The salt of claim 2, selected from the group consisting essentially of:
acetyl L-carnitine L-isoleucinate hydrochloride,
propionyl L-carnitine L-leucinate hydrochloride,
L-carnitine L-valinate phosphate,
acetyl L-carnitine L-cysteinate hydrochloride,
acetyl L-carnitine L-arginate dihydrochloride,
acetyl L-carnitine L-glutamninate hydrochloride,
acetyl L-carnitine L-asparaginate hydrochloride,
acetyl L-carnitine glycinate hydrochloride,
acetyl L-carnitine L-alaninate hydrochloride,
acetyl L-carnitine L-threoninate hydrochloride,
acetyl L-carnitine L-serinate hydrochloride,
propionyl L-carnitine L-prolinate hydrochloride,
L-carnitine L-hystidinate hydrochloride,
L-carnitine L-methionate hydrochloride,
propionyl L-carnitine L-phenylalaninate hydrochloride, and
acetyl L-carnitine L-typtophanate hydrochloride.

5. A composition comprising a compound of claim 1, as active ingredient, and at least a further component selected from pharmacologically acceptable excipients and active ingredients.

6. A composition comprising a compound of claim 4, as active ingredient, and at least a further component selected from pharmacologically acceptable excipients and active ingredients.

7. The composition of claim 5, in the form of tablets, chewable tablets, capsules, granulates or powders.

8. The composition of claim 5, in unit dosage form, comprising as active ingredient a salt of L-carnitine or alkanoyl L-carnitine of formula (I) comprising 50–2,000 mg of L-carnitine, alkanoyl L-carnitine respectively, as inner salts.

9. The composition of claim 5 for human use, as dietary supplement, dietetic product or drug.

10. The composition of claim 5 for veterinary use as supplement for fodders.

11. The composition of claim 8, wherein the active ingredient comprises 100 to 1,000 mg of L-carnitine, alkanoyl L-carnitine, as inner salts.

* * * * *